United States Patent [19]

Schön et al.

[11] Patent Number: 5,008,246

[45] Date of Patent: Apr. 16, 1991

[54] PEPTIDES SUPPRESSING THE FUNCTION OF THE IMMUNE SYSTEM, PHARMACEUTICAL COMPOSITIONS CONTAINING THEM AND PROCESS FOR PREPARING SAME

[75] Inventors: Istvan Schön; Olga Nyeki; Lajos Kisfaludy, deceased, late of Budapest, by Maria Kisfaludy, Marta Kisfaludy, Andras Kisfaludy, legal heirs; Laszlo Denes; György Hajos; Laszlo Szporny, all of Budapest, Hungary

[73] Assignee: Richter Gedeon Vegyeszeti Gyar R. T., Budapest, Hungary

[21] Appl. No.: 365,457

[22] Filed: Jun. 13, 1989

[30] Foreign Application Priority Data

Jun. 14, 1988 [HU] Hungary ............................... 3037/88

[51] Int. Cl.$^5$ ........................ A61K 37/02; C07K 5/08; C07K 5/10
[52] U.S. Cl. .................................... 514/18; 530/330; 530/331
[58] Field of Search .................. 514/18; 530/330, 331, 530/332

[56] References Cited

U.S. PATENT DOCUMENTS 4,505,853  3/1985  Goldstein et al. .................. 530/330

OTHER PUBLICATIONS

Denes et al., Chem. Abstracts. 107(19):169209p.
Szokan et al., 7th Int. Symp. on HPLC of Prot., Pep., & Polynuc. II, Nov. 2-4, 1987, pp. 115-122.
Denes et al., Therapeutic Possibilities of Thympoietin Fragments (TP 3 and TP 4) Based on Experimental Animal Models, Drugs Exptl. Clin. Res., XIII (5), 279-287 (1987).
Görög et al., II. Detection and Quantification of a Diastereomeric Impurity in the Peptide RGH-0205 (Arg-Lys-Asp), Journal of Chromatography, 452, pp. 317-321.

Primary Examiner—Lester L. Lee
Assistant Examiner—Stephen B. Maebius
Attorney, Agent, or Firm—Herbert Dubno; Jonathan Myers

[57] ABSTRACT

The invention relates to novel peptides and their acid addition salts, suppressing the function of the immune system, pharmaceutical compositions containing these peptides as well as to a process for preparing these peptides and compositions. The peptides are represented by formulae (1) to (16):

| | |
|---|---|
| D—Arg—Lys—D—Asp, | (1) |
| Arg—D—Lys—Asp, | (2) |
| D—Arg—D—Lys—D—Asp, | (3) |
| Arg—D—Lys—D—Asp, | (4) |
| D—Arg—Lys—Asp, | (5) |
| D—Arg—D—Lys—Asp, | (6) |
| Arg—Lys—D—Asp, | (7) |
| Arg—Lys—D—Asp—Val, | (8) |
| Arg—Lys—Asp—D—Val, | (9) |
| D—Arg—Lys—Asp—Val, | (10) |
| Arg—D—Lys—Asp—Val, | (11) |
| Lys(Arg)—Asp, | (12) |
| Lys(Arg)—D—Asp, | (13) |
| Arg—Lys(Arg)—Asp, | (14) |
| Arg—Lys—Asp(Val), | (15) |
| and | |
| Arg—Lys—D—Asp(Val) | (16) |

The novel peptides are useful for the therapy of diseases where a decrease in the activity of the immune system is desirable.

9 Claims, No Drawings

PEPTIDES SUPPRESSING THE FUNCTION OF THE IMMUNE SYSTEM, PHARMACEUTICAL COMPOSITIONS CONTAINING THEM AND PROCESS FOR PREPARING SAME

FIELD OF THE INVENTION

This invention relates to novel peptides of formulae (1) to (16)

| | |
|---|---|
| D—Arg—Lys—D—Asp, | (1) |
| Arg—D—Lys—Asp, | (2) |
| D—Arg—D—Lys—D—Asp, | (3) |
| Arg—D—Lys—D—Asp, | (4) |
| D—Arg—Lys—Asp, | (5) |
| D—Arg—D—Lys—Asp, | (6) |
| Arg—Lys—D—Asp, | (7) |
| Arg—Lys—D—Asp—Val, | (8) |
| Arg—Lys—Asp—D—Val, | (9) |
| D—Arg—Lys—Asp—Val, | (10) |
| Arg—D—Lys—Asp—Val, | (11) |
| Lys(Arg)—Asp, | (12) |
| Lys(Arg)—D—Asp, | (13) |
| Arg—Lys(Arg)—Asp, | (14) |
| Arg—Lys—Asp(Val), | (15) |
| and | |
| Arg—Lys—D—Asp(Val) | (16) | their acid addition salts and pharmaceutical compositions containing these piptides.

According to an other aspect of the invention, there is provided a process for the preparation of the novel peptides of formulae (1) to (16) and pharmaceutical compositions containing them.

The peptides of the above formulae (1) to (16) are capable of inhibiting certain partial processes of the immune system.

The invention further relates to a method of treating mammals including human for suppressing the function of the immune system by using the above peptides or compositions containing them.

BACKGROUND OF THE INVENTION

The compounds according to the invention are the derivatives and diastereomers of the active center of thymopoietin. However, while the known peptides Arg-Lys-Asp, Arg-Ly-Asp-Val (Hungarian patent specification No. 185,263) and Arg-Lys-Asp-Val-Tyr (Hungarian patent specification No. 183,579), considered to be the active center of thymopoietin, exert a significant immunostimulating effect [Drugs of the Future 11, 764 (1986); and Drugs of Today 22, 17 (1986)], the peptides according to the present invention show instead the opposite action.

It is known that the causes or accompanying syndromes of several diseases can be traced back to disturbances of the dynamical function of the immune system. Immunostimulants are used for healing of hereditary, native (after-birth or after-parturition, old age) and acquired immunodeficiency diseases (e.g. after infections and operations, AIDS, etc.). However, there exists a number of diseases or state which can be attributed to the increased or temporarily undesired function of the immune system resulting in the spontaneous modification of the defense mechanism of the organism. In autoimmune diseases, the defense system is not capable of distinguishing the "own" from the "exogenous," thus, it protects itself by producing antibodies against its own antigen too, whereby severe consequences occur. Allergy diseases are accompanied by an increased production of antibodies caused by exogenous substances. The rejecting reaction following organ transplants is also a consequence of the normal and healthy function of the organism which, however, should temporarily by suspended for allowing the transplanted foreign organ to be built into the organism.

Cyclophosphamide [2-[bis(2-chloroethyl)amino]tetrahydro-2H-1,3,2-oxazaphosphorine-2-oxide], azathioprin [6-(1-methyl-4-nitro-5-imidazolylthio)purine] and corticosteroids used for treating the autoimmune diseases as well as H-1 receptor-blocking antihistamines used for treating allergies, and cyclosporin, being an indispensable drug for organ transplants belong to the immunosuppressive agents inhibiting the increased function or weakening the normal function of the immune system.

A number of accompanying side effects can be explained by the relatively low therapeutic index (<10) of the immunosuppressive drugs. Thus, they can be administered only under exact medical control and, in general, only for a limited period. A particular advantage of the peptide-type active agents consists in their extraordinarily high therapeutic index (>100 to 1000), i.e. their dose inducing a harmful effect is several orders of magnitude higher than their effective dose; under physiological conditions, they are very rapidly decomposed and do not accumulate in the organism. Their effect is based on their ability to undergo complicated reactions with a high efficiency during their short life.

SUMMARY OF THE INVENTION

It has been found that the novel, D-amino acid-containing diastereomers of the Arg-Lys-Asp and Arg-Lys-Asp-Val immunostimulating peptides of formulae (1) to (16) including the so-called isopeptides bearing arginine on the α- or α- and β-amino groups of lysine as well as containing valine on the β-carboxyl group of aspartic acid show a suppressing effect in several immunological tests, although, according to knowledge available up to now (see e.g. the U.S. Pat. No. 4,505,853), the modifications of both types are usually rather accompanied by an increase in the resistance to enzymes, by an enhancement of the peptide stability and by a longer duration of the original biological effect.

The novel peptides of formulae (1) to (16) of the invention are prepared by stepwise chain-lengthening in solution successively employing coupling steps of active ester method and/or mixed anhydride method known in peptide chemistry, furthermore α-amino group and/or α- and ε-amino group deliberating steps whereby (a) starting with carboxy-terminal amino acid derivatives containing a carboxy group esterified by a group being removable by hydrogenation or acidolysis, optionally a protected side-chain amino group and/or a carboxy group esterified by a group being removable by hydrogenation or acidolysis, and a free amino group, derivatives of the novel peptides of formulae (1) to (16) esterified on their carboxy groups and containing protecting groups Boc and/or Z on their amino groups not involved in the peptide linkage are prepared, (b) then removing the protecting groups being present by catalytic hydrogenation and/or acidic treatment and, (c) if desired, converting the free peptides of formulae (1) to (16) to their acid addition salts by treating them with an acid.

In the synthesis, such a combination of protective groups is used, which makes possible to remove selectively the amino-protecting group then to cleave all the protective groups possibly in one single step at the end of the synthesis. In order to form the succinimide esters [—O—Su] (E. Wünsch; Synthese von Peptiden, Vol. 2., Georg Thieme Verlag, Stuttgart, 1974, page 149), the pentafluorophenyl esters (Hungarian patent specification No. 168,431), or mixed anhydrides (Hungarian patent specification No. 183,579) is used.

For protecting amino moieties Boc or Z group, for protecting carboxyl groups esterification with tert.-butyl-, benzyl or nitrobenzyl alcohol are preferably employed. The Z stands for benzyloxycarbonyl and the Box stands for t-butoxycarbonyl.

After completion of the synthesis, the optionally present protecting group(s) is (are) removed from the protected peptide thus obtained then, if desired, the free peptide is converted to its acid addition salt by treating with an acid. For removing the protective groups, catalytic hydrogenation or acidolysis is used.

The free peptides obtained are usually sufficiently pure for therapeutical use and do not require any further purification. However, if desired, then can be purified by chromatography on a silica gel column. A peptide obtained in the form of a solution can be isolated by evaporation or lyophilization of the solution. The free peptide can be converted optionally to a salt; it is preferred to transform it to an acid addition salt with a pharmaceutically acceptable acid such as e.g. hydrochloric, sulfuric, phosphoric, acetic and citric acid.

The immunosuppressive effect of the prepared compounds was investigated by using the methods described hereinafter.

1. Effect on the antibody-producing cells

This investigation was carried out with splenocytes obtained from newborn rats according to the method of Canningham (Handbook of Experimental Immunology, Ed. D. M. Weir, Vol. 2., Blackwell, Oxford-London, page 285, 1978). Twelve Wistar rats arising from a single litter were intraperitoneally (i.p.) treated with 25 µg of test substance within 12 hours following their birth. On the 14th day after birth, the animals were i.p. immunized by 0.5 ml of a suspension containing 5% sheep erythrocyte, then bled by decapitation after 7 days. From the splenocytes obtained from the animals, a homogeneous suspension was prepared with the sheep erythrocyte suspension and complement which was then put into a chamber, suitable to obtain a monocellular layer. Around the antibody-producing splenocytes, lytic areas, the so-called plaques were formed. The data summarized in Table 1 illustrates the effect of the treatment with the suppressive substances. The change in the count of the plaque-forming cells under effect of the treatment is given as a percentage in the Table. (The cell count obtained from untreated animals was used as control.) In the case of known immunostimulating substances (see compound "A", "B" and "C" in Table 1), this percentage is significantly increased.

TABLE 1

| | Suppression of the antibody production | |
|---|---|---|
| No./symbol | Peptide | Change in the plaque formation % |
| 1 | D—Arg—Lys—D—Asp | −17 |
| 2 | Arg—D—Lys—Asp | −11 |
| 3 | D—Arg—D—Lys—D—Asp | −13 |

TABLE 1-continued

| | Suppression of the antibody production | |
|---|---|---|
| No./symbol | Peptide | Change in the plaque formation % |
| 4 | Arg—D—Lys—D—Asp | −16 |
| 5 | D—Arg—Lys—Asp | −44 |
| 6 | D—Arg—D—Lys—Asp | −41 |
| 7 | Arg—Lys—D—Asp | −43 |
| A | Arg—Lys—Asp | +71 |
| B | Arg—Lys—Asp—Val | +60 |
| C | Arg—Lys—Asp—Val—Tyr | +62 |

2. Effect on the primary antibody production

These examinations were carried out on male CFLP (LATI) mice with 23 to 30 g body-weight. The animals were i.p. immunized by 0.5 ml of a suspension containing 1% sheep erythrocyte washed 3 times, then the animals were i.p. treated with a 100 mg/kg dose of the test substances. On the 3rd day following the treatment, 0.60 to 0.70 ml of blood each was taken from the animals. After standing for 30 minutes, the sera were separated by centrifuging and the haemagglutination titre was determined according to the method of Takatsy [Acta Microbiol. Acad. Sci. Hung. 3, 191 (1955)]. The data are summarized in Table 2 showing the percentage of the suppressing (inhibitory) effect on the primary antibody production in relation to the untreated animals. The immunostimulating compounds "B" and "C" possess an opposite action in the same test.

TABLE 2

| | Effect on the primary antibody production | |
|---|---|---|
| No./symbol | Peptide | Effect on the primary antibody production % |
| 4 | Arg—D—Lys—D—Asp | −15 |
| 5 | D—Arg—Lys—Asp | −15 |
| 11 | Arg—D—Lys—Asp—Val | −20 |
| B | Arg—Lys—Asp—Val | +31 |
| C | Arg—Lys—Asp—Val—Tyr | +29 |

3. Effect on the phagocytating capacity of resting macrophages

These examinations were carried out on 6 months old male NZB (OLAC-SzKB) mice according to the method described in J. Immunopharmnacol. 4, 265 (1982–1983). The animals were treated daily with a 1 mg/kg subcutaneous (s.c.) dose of the test substances for 4 days. After bleeding the animals, their peritonea were washed with 8 ml of PBS buffer solution (pH 7.2) each containing 10 IU of heparin. The cell suspension washed out from the peritoneum was made free of the erythrocytes by shocking with distilled water, then washed 3 times with PBS buffer solution. The sedimentation between two washings was achieved by centrifuging at 1000 rpm for 5 minutes. Then, the concentration of each cell suspension was adjusted to $10^6$ cell/ml and the suspension was settled for 30 minutes in a Boyden-chamber at 37° C. in an atmosphere containing 5% of carbon dioxide. Over the macrophages adhered to the glass wall, opsonized yeast was layered. After removing the non-phagocytated particles, those incorporated by the macrophages were counted in each cell. In Table 3, the percentage of decrease in the count of the phagocytated yeast cells is given in relation to the macrophages isolated from the untreated animals as control.

TABLE 3

Effect on the phagocytating capacity of resting macrophage cells

| No./symbol | Peptide | Effect on the phagocytating capacity of resting macrophages % |
|---|---|---|
| 1 | D—Arg—Lys—D—Asp | −41 |
| 2 | Arg—D—Lys—Asp | −63 |
| 6 | D—Arg—D—Lys—Asp | −11 |
| 7 | Arg—Lys—D—Asp | −21 |
| 8 | Arg—Lys—D—Asp—Val | −14 |
| 10 | D—Arg—Lys—Asp—Val | −25 |
| 11 | Arg—D—Lys—Asp—Val | −19 |
| 12 | Lys(Arg)—Asp | −42 |
| 13 | Lys(Arg)—D—Asp | −50 |

4. Inhibition of the contact dermatitis

These investigations were carried out on male BALB/c (LATI) mice with 20 to 22 g body-weight by using the method of Evans et al. [Br. J. Pharmacol. 43, 403 (1971)]. The abdominal side of the animals were depilated, then the naked abdominal skin of each animal was sensitized by 0.1 ml of the oxazolone solution of 2% in sunflower oil. After 1 week, the mice were i.p. treated with an 1.0 mg/kg dose of the test substance (dissolved in physiological saline solution), then the right ear of the animals was directly treated with 10 μl of an acetone solution containing 2% oxazolone while their left ear was treated with 10 μl of acetone. After 24 hours, their ears were cut off and weighed. The difference between the weight of treated and untreated ears of the animals was compared with the difference observed at the animals treated with the test substance and treated only with physiological saline solution, respectively. The difference in the ear weight was considered to be proportional to the extent of the contact dermatitis, while the value measured at the animals not treated with the test substance was taken as control, the dermatitis-diminishing effect of the test substances was obtained as expressed in percentage shown in Table 4.

TABLE 4

Inhibition of the contact dermatitis

| No./sumbol | Peptide | Inhibition of the contact dermatitis % |
|---|---|---|
| 2 | Arg—D—Lys—Asp | −22 |
| 3 | D—Arg—D—Lys—D—Asp | −31 |
| 4 | Arg—D—Lys—D—Asp | −19 |
| 5 | D—Arg—Lys—Asp | −35 |
| 6 | D—Arg—D—Lys—Asp | −19 |
| 7 | Arg—Lys—D—Asp | −34 |
| 9 | Arg—Lys—Asp—D—Val | −16 |
| 12 | Lys(Arg)—Asp | −16 |

The peptides according to the invention and their acid addition salts may be formulated in the common pharmaceutical compositions for therapeutical use, to decrease the activity of the immune system. The advantage of using the novel compounds consists in their nearly complete safety since they have no side effect in the dose range used.

The peptides of the formulae (1) to (16) are used alone, in their free or acid addition salt form but suitably in a pharmaceutical formulation. These formulations may be solid, liquid or semiliquid and can be prepared by using fillers, diluents, stabilizers, pH and osmotic pressure-influencing agents as well as additives promoting the formulation commonly used in such formuations.

The solid pharmaceutical compositions may be e.g. powder ampoules, suitable for preparing injection solutions. Injectable compositions and infusions are liquid.

The pharmaceutical composition according to the invention is administered to the patient in an amount containing the dose required of the active ingredient to achieve the desired effect. This dose depends on the severity of the disease, body-wight of the patient, sensitivity of the patient to the active ingredient, route of administration and the number of daily treatments. THe dose to be used in any case can be defined by the physician knowing the patient to be treated.

For a simple administration, the pharmaceutical compositions consist of dosage units containing the active ingredient to be once administered or a half, third or fourth or a low-number multiplet thereof.

The compositions according to the invention usually contain 1 to 100 mg of active ingredient per dosage unit. However, in some compositions, the amount of the active ingredient may of course be higher or lower than the limits defined above.

The invention is illustrated in detail by the following non-limiting Examples. The abbreviations used in the description correspond to those in general accepted in the literature [Biochem. J. 219, 345 (1984)]. According to the usual practice, the "D" configuration is only indicated in the name given by sympols; other amino acids have "L" configuration. The melting points were determined in a Dr. Tottoli device (manufactured by Büchi, Switzerland). Thin layer chromatography examinations were carried out by using a ready-for-use adsorbent (DC-Fertigplatten, manufactured by Merck, FRG) and the following solvent mixtures (where the "stock solution" is a 20:6:11 mixture of pyridine/acetic acid/water):

1. ethyl acetate/stock solution, 19:1;
2. ethyl acetate/stock solution, 9:1;
3. ethyl acetate/stock solution, 6:1;
4. ethyl acetate/stock solution, 7:3;
5. n-butanol/stock solution, 3:7;
6. n-butanol/stock solution, 1:4; and
7. n-butanol/acetic acid/ethyl acetate/water, 1:1:1:1.

(The ratios are given in volume-ratio values).

The chromatograms were detected by ninhydrin or, after chlorination, by using the potassium iodide/tolidine reagent.

The high performance liquid chromatography (HPLC) analyses were carried out by using a device equipped with a labor MIM 308 type UV detector with variable wave-length, Labor-MIM Loop injector, feeding pump consisting of Gilson 802C and 302 units, pressure-measuring device as well as a Radelkis OH 827 type recorder. For the separation, $C_{18}$-phase Labor-MIM type charge of 150 cm in length, 4.6 mm in inner diameter with a particle size of 6 μm was used. An aqueous phosphoric acid solution at a concentration of 0.2% adjusted to pH 8 by adding ammonia solution of a concentration of 10% was employed for elution of tripeptides, whereas this eluent was completed with 10% by volume of acetonitrile for elution of tetrapeptides. The measurement was accomplished at a flow rate of 1 ml/min, when the absorption of the solution was detected at 212 mm. The chromatograms were evaluated by area-normalization. The purity of the target compounds was higher than 95% based on both HPLC and thin layer chromatography (TLC) analysis.

The specific optical activity was determined in a Perkin-Elmer 241 type polarimeter. All solvents were removed or evaporated in a Büchi rotating evaporator in a water bath at 40° C.

The $^1$H-NMR and $^{13}$C-NMR spectra of the intermediates and target compounds were determined in a Varian XLA 400 type device. The target compounds were dissolved in all cases in $D_2O$. The spectra were in agreement with the structure expected.

The amino acid analysis of the target compounds was carried out in a Biotronik LC 5001 type equipment. The samples were hydrolyzed in a hydrochloric acid solution of 6 molar concentration at 110° C. for 24 hours. The results of the analyses were in all cases within an error limit of ±5%.

The starting substances of the syntheses are commonly known in the literature. The D-antipodes were synthetized starting with D amino acids in the same way as the L-antipodes.

Example 1

Preparation of Arg-Lys-D-Asp (method "A")

4.06 ml (29.0 mmol) of triethylamine are added to a mixture containing 6.60 g (13.8 mmol) of Z-Lys(Boc)-OSu and 4.86 g (14.5 mmol) of H-D-Asp(O$^t$Bu)-O$^t$Bu oxalate in 60 ml of ethyl acetate, then the mixture is left to stand overnight. Then, it is successively washed with 20 ml of water, 3 times with 20 ml of 1 molar hydrochloric acid each, 3 times with 20 ml of 5% aqueous potassium hydrogenocarbonate solution each, and finally with 20 ml of water. The organic layer is dried on anhydrous sodium sulfate and evaporated under reduced pressure.

The evaporation residue which is an oily product (weighing 6.5 g, $R_f^2=0.8$), i.e. the protected depeptide is dissolved in 70 ml of methanol, 1.5 g of palladium-on-carbon are added and gaseous hydrogen is bubbled through the suspension under stirring for 2 hours. The mixture is filtered and 1.45 g (11.5 mmol) of oxalic acid dihydrate are added to the filtrate. After evaporation, the residue is triturated with ether and the suspension obtained is filtered to give 4.80 g of free Lys-D-Asp oxalate, m.p.: 118°–121° C., $[\alpha]_D^{20}=11.0°$ (c=1, methanol), $R_f^2=0.25$.

0.78 ml (6.0 mmol) of isobutyl chloroformate is dropwise added to a solution containing 1.98 g (6.0 mmol) of Boc-Arg(.HCl)-OH.H$_2$O and 0.67 ml (6.0 mmol) of N-methylmorpholine in 20 ml of dimethylformamide (DMF) cooled to −10° C. The mixed anhydride thus obtained is stirred at −10° C. for 10 minutes, then a solution containing 3.27 g (5.8 mmol) of Lys-D-Asp oxalate prepared as described above and 1.28 ml (11.6 mmol) of N-methylmorpholine in 15 ml of DMF cooled to −10° C. are added. Thereafter, the reaction mixture is left to warm to room temperature and set aside overnight. The solvent is evaporated under reduced pressure, the residue is dissolved in 50 ml of chloroform and successively washed 3 times with 20 ml of 1 molar hydrochloric acid each and 20 ml of water, then dried on anhydrous sodium sulfate. After filtering the suspension, the filtrate is evaporated under reduced pressure. The only residue is solidifying by adding diisopropyl ether. The suspension is filtered and the filtrate is evaporated to obtain 3.20 g (4.18 mmol) of amorphous Boc-Arg(.HCl)-Lys(Boc)-D-Asp(O$^t$Bu)-O$^t$Bu tripeptide ester salt, $R_f^3=0.10$, $R_f^4=0.45$, $[\alpha]_D^{20}=-6.4°$ (c=1, methanol).

Other protected peptides prepared as described above are listed in Table 5.

1.60 g (2.08 mmol) of the protected tripeptide ester salt obtained as described above are treated with 20 ml of trifluoroacetic acid for 2 hours, then evaporated under reduced pressure. After solidifying the residue by adding ether, the suspension is filtered and the precipitate is thoroughly washed with ether. The trifluoroacetate salt obtained is dissolved in 20 ml of water and 5 ml of Dowex 2×8 ion-exchanged resin of acetate phase (manufactured by the Dow Chemical Co.) are added. After 30 minutes, the suspension is filtered, the filtrate is evaporated under reduced pressure and the evaporation residue is solidified by adding methanol to yield 1.0 g of amorphous Arg-Lys-D-Asp.CH-COOH tripeptide acetate, $[\alpha]_D^{20}=+1.0°$ (c=1.0, 10% acetic acid). Amino acid analysis: D-Asp=1.03, Lys=1.00, Arg=0.98.

The physical constants of the target compounds of formulae (1) to (16) prepared as described above are summarized in Table 6.

Example 2

Preparation of Lys(Arg)-Asp (method "B")

3.08 ml of triethylamine are added to a mixture containing 4.77 g (10.0 mmol) of Boc-Lys(Z)-OSu and 3.69 g (11.0 mmol) of H-Asp(O$^t$Bu)-O$^t$Bu oxalate in 60 ml of ethyl acetate and the mixture is reacted overnight. Then, the mixture is successively washed with 20 ml of water, 3 times with 20 ml of 1 molar hydrochloric acid each, 3 times with 5% potassium hydrogenocarbonate solution each, and finally with 20 ml of water, dried on anhydrous sodium sulfate, then evaporated under reduced pressure.

5.6 g of the protected dipeptide thus obtained as an oil ($R_f^4=0.85$) are dissolved in 60 ml of methanol and after adding 1.0 g of palladium-on-carbon catalyst, gaseous hydrogen is bubbled through the suspension under stirring for 2 hours. Then the suspension is filtered, 1.1 g of oxalic acid dihydrate are added to the filtrate and the solvent is evaporated. The crystalline residue is suspended in ether, filtered and dried to give 4.4 g of Boc-Ly-Asp(O$^t$Bu)-O$^t$Bu oxalate, m.p.: 135°–138° C., $R_f^4=0.35$.

The oxalate salt obtained is acylated at the $\epsilon$-amino group of Lys by the mixed anhydride coupling method, as described in Example 1, then the protecting groups are removed from the protected tripeptide thus obtained as described also in Example 1.

The physical constants of the protected and free peptides obtained as described above are summarized in Tables 5 and 6.

Example 3

Preparation of Arg-Lys(Arg)-Asp (method "C")

1.85 g (5.5 mmol) of H-Asp(O$^t$Bu)-O$^t$Bu oxalate are suspended in 50 ml of ether in a shaking funnel and 20 ml of 5% potassium hydrogenocarbonate solution are added to the suspension. The mixture is shaken until the complete dissolution, the aqueous phase is separated and the ethereal phase is washed with 20 ml of 5% potassium hydrogenocarbonate solution and with 20 ml of water, dried on anhydrous sodium sulfate and concentrated to a volume of 20 ml under reduced pressure. After adding 2.49 g (6.0 mmol) of protected lysine Z-Lys(Z)-OH and cooling to 0° C., 1.20 g (5.8 mmol) of dicyclohexylcarbodimide are added. The mixture is maintained at 0° C. for 30 minutes, then left to stand at room temperature overnight. The dicyclohexylurea precipitate is filtered off, the filtrate is successively washed 3 times with 10 ml of 1 molar hydrochloric acid each, 3 times with 10 ml of 5% sodium hydrogenocarbonate solution each, and finally with 20 ml of water and after drying on anhydrous sodium sulfate, it is evaporated under reduced pressure.

3.0 g of the protected dipeptide ($R_f{}^2 = 0.80$) obtained as an oily evaporation residue are dissolved in 50 ml of methanol and after adding 1.0 g of palladium-on-carbon catalyst, gaseous hydrogen is bubbled through the suspension for 2 hours. After filtering off the catalyst, 1.18 g (9.34 mmol) of oxalic acid dihydrate are added to the filtrate and the mixture is concentrated to 10 ml under reduced pressure. The suspension thus obtained is diluted to 100 ml by adding ether, the precipitate is filtered and washed with ether. Thus, 1.49 g of H-Lys-Asp(O$^6$Bu)-O$^t$Bu oxalate ($R_f{}^5 = 0.25$) are obtained which are acylated on both amino groups of the lysine moiety by using the mixed anhydride coupling method as described in Example 1. The protecting groups are removed from the protected tetrapeptide thus obtained as described also in Example 1.

The physical constants of the protected and free tetrapeptides are summarized in Tables 5 and 6.

Example 4

Preparation of D-Arg-Lys-Asp-Val (method "D")

After adding 4.2 ml (30 mmol) of triethylamine to a suspension of 6.3 g (30 mmol) of H-Val-O$^t$Bu.HCl and 11.2 g (26.8 mmol) of Z-Asp(O$^t$Bu)-Osu in 110 ml of dimethylformamide, the mixture is set aside overnight, then evaporated under reduced pressure. The oily evaporation residue is dissolved in 200 ml of ethyl acetate and successively washed twice with 40 ml of 1 molar hydrochloric acid each, 40 ml of water, 40 of 5% sodium hydrogenocarbonate solution, and gain with 40 ml of water. After drying on anhydrous sodium sulfate, the solution is filtered and the filtrate is evaporated under reduced pressure.

13.0 g of the protected dipeptide ($R_f{}^1 = 0.80$) obtained as an evaporation residue are dissolved in 100 ml of methanol and after adding 1.5 g of palladium-on-carbon catalyst, gaseous hydrogen is bubbled through the suspension under stirring for 2 hours. After filtering off the catalyst, the filtrate is evaporated under reduced pressure. The oily evaporation residue is dissolved in 100 ml of ether and methanolic hydrogen chloride solution is added until the pH is adjusted to 5. The suspension thus obtained is cooled for 5 hours, then filtered, the precipitate is washed with ether and dried to give 9.0 g (88.0 mmol) of H-Asp(O$^t$Bu)-Val-O$^t$Bu.HCl, m.p.: 187°-189° C., $R_f{}^1 = 0.40$.

Further on, the process described in Examples 1 is followed.

The physical constants of the protected and free tetrapeptides thus obtained are summarized in Tables 5 and 6.

Example 5

Preparation of Arg-Lys-Asp(Val) (method "E")

After adding 1.68 ml (12.0 mmol) of triethylamine to a suspension containing 2.58 g (12.0 mmol) of H-Val-O$^t$Bu.HCl and 4.62 g (11.0 mmol) of Z-Asp(OSu)-O$^t$Bu in 25 ml of DMF, the mixture is reacted overnight, then evaporated under reduced pressure. The solution of the evaporation residue in 50 ml of ethyl acetate is successively washed with 20 ml of water, 3 times with 20 ml of 1 molar hydrochloric acid each, 3 times with 20 ml of 5% sodium hydrogenocarbonate solution each, and finally with 20 ml of water, the organic phase is dried on anhydrous sodium sulfate and evaporated under reduced pressure to obtain 4.3 g (81.7%) of protected dipeptide, m.p.: 86.5°-87.0° C., $R_f{}^1 = 0.85$.

After adding 1.0 g of palladium-on-carbon catalyst to a solution containing 4.07 g (8.5 mmol) of the protected dipeptide obtained above in 40 ml of methanol, the suspension is hydrogenated by bubbling gaseous hydrogen through the suspension while stirring for 2 hours. After filtering off the catalyst, the filtrate is evaporated under reduced pressure. The evaporation residue is dissolved in 50 ml of ether and 0.76 g (8.5 mmol) of oxalic acid dihydrate dissolved in 3 ml of methanol is added to yield 3.37 g (91.6%) of free dipeptide oxalate, m.p.: 142°-143° C., $R_f{}^1 = 0.15$, which is then acylated as described in Example 1.

The physical constants of the protected and free tetrapeptides thus obtained are summarized in Tables 5 and 6.

TABLE 5

| | Physical constants of protected peptides | | | | |
|---|---|---|---|---|---|
| No. | Name | Method | $[\alpha]_D^{20}$ | $R_f{}^3$ | $R_f{}^4$ | $R_f{}^5$ |
| I | Boc—D—Arg(.HCl)—Lys(Boc)—D—Asp(O$^t$Bu)—O$^t$Bu | A | −0.6°(a) | 0.1 | 0.45 | |
| II | Boc—Arg(.HCl)—D—Lys(Boc)—Asp(O$^t$Bu)—O$^t$Bu | A | −1.4°(a) | 0.1 | 0.45 | |
| III | Boc—D—Arg(.HCl)—D—Lys(Boc)—D—Asp(O$^t$Bu)—O$^t$Bu | A | +19.8°(a) | 0.1 | 0.45 | |
| IV | Boc—Arg(.HCl)—D—Lys(Boc)—D—Asp(O$^t$Bu)—O$^t$Bu | A | +11.8°(a) | 0.1 | 0.45 | |
| V | Boc—D—Arg(.HCl)—Lys(Boc)—Asp(O$^t$Bu)—O$^t$Bu | A | −12.4°(a) | 0.1 | 0.45 | |
| VI | Boc—D—Arg(.HCl)—D—Lys(Boc)—Asp(O$^t$Bu)—O$^t$Bu | A | +5.6°(a) | 0.1 | 0.45 | |
| VII | Boc—Arg(.HCl)—Lys(Boc)—D—Asp(O$^t$Bu)—O$^t$Bu | A | −5.6°(a) | 0.1 | 0.45 | |
| VIII | Boc—Arg(.HCl)—Lys(Boc)—D—Asp(O$^t$Bu)—Val—O$^t$Bu | A+D | +3.1°(b) | 0.25 | | |
| IX | Boc—Arg(.HCl)—Lys(Boc)—Asp(O$^t$Bu)—D—Val—O$^t$Bu | A+D | −34.5°(b) | 0.25 | | |
| X | Boc—D—Arg(.HCl)—Lys(Boc)—Asp(O$^t$Bu)—Val—O$^t$Bu | A+D | −22.6°(b) | 0.25 | | |
| XI | Boc—Arg(.HCl)—D—Lys(Boc)—Asp(O$^t$Bu)—Val—O$^t$Bu | A+D | −10.8°(b) | 0.25 | | |
| XII | Boc—Lys/⁻Boc—Arg(.HCl)_7—Asp(O$^t$Bu)—O$^t$Bu | A+B | | 0.30 | | |
| XIII | Boc—Lys/⁻Boc—Arg(.HCl)_7—D—Asp(O$^t$Bu)—O$^t$Bu | A+B | −12.0°(a) | 0.05 | 0.35 | |
| XIV | Boc—Arg(.HCl)—Lys/⁻Boc—Arg(.HCl)_7—Asp(O$^t$Bu)—O$^t$Bu | A+C | −15.0°(c) | | | 0.20 |
| XV | Boc—Arg(.HCl)—Lys(Boc)—Asp(Val—O$^t$Bu)—O$^t$Bu | A+E | −14.6°(b) | 0.25 | | |
| XVI | Boc—Arg(.HCl)—Lys(Boc)—D—Asp(Val—O$^t$Bu)—O$^t$Bu | A+E | −22.6°(a) | 0.30 | | |

The numbering (by Roman numerals) of the protected compounds agrees with the (Arabic) numbers of the target compounds in Table 6.
(a): c=1, methanol; (b): C=1, dimethylformamide; (c): c=0.6, methanol.

TABLE 6

| | | Physical constants of free peptides | | | | |
|---|---|---|---|---|---|---|
| No. | Name | $[\alpha]_D^{20}$ 10% AcOH | (c=1) AcOH | (5) | $R_f$ (6) | (7) |
| 1 | D—Arg—Lys—D—Asp | −33.2° | | | 0.15 | 0.08 |
| 2 | Arg—D—Lys—Asp | +33.2° | | | 0.15 | 0.08 |
| 3 | D—Arg—D—Lys—D—Asp | −3.4° | −9.2° | | 0.15 | 0.08 |
| 4 | Arg—D—Lys—D—Asp | +35.0° | +24.0° | | 0.15 | 0.08 |
| 5 | D—Arg—Lys—Asp | −33.8° | −24.4° | | 0.15 | 0.08 |
| 6 | D—Arg—D—Lys—Asp | −1.2° | +6.2° | | 0.15 | 0.08 |
| 7 | Arg—Lys—D—Asp | +1.0° | | | 0.15 | 0.08 |
| 8 | Arg—Lys—D—Asp—Val | +13.7° | | 0.15 | | 0.10 |
| 9 | Arg—Lys—Asp—D—Val | −7.3° | | 0.15 | | 0.10 |
| 10 | D—Arg—Lys—Asp—Val | −47.7° | | 0.15 | | 0.10 |
| 11 | Arg—D—Lys—Asp—Val | +13.1° | | 0.15 | | 0.10 |
| 12 | Lys(Arg)—Asp | | +16.4° | | 0.20 | 0.12 |
| 13 | Lys(Arg)—D—Asp | | +19.4° | | 0.20 | 0.12 |
| 14 | Arg—Lys(Arg)—Asp | | +12.7° | | 0.05 | 0.05 |
| 15 | Arg—Lys—Asp(Val) | +2.9° | | | 0.20 | 0.10 |
| 16 | Arg—Lys—D—Asp(Val) | −12.0° | | | 0.20 | 0.10 |

We claim:

1. A peptide of the formulae (1) to (16) D-Arg-Lys-D-Asp,

| | |
|---|---|
| D—Arg—Lys—D—Asp, | (1) |
| Arg—D—Lys—Asp, | (2) |
| D—Arg—D—Lys—D—Asp, | (3) |
| Arg—D—Lys—D—Asp, | (4) |
| D—Arg—Lys—Asp, | (5) |
| D—Arg—D—Lys—Asp, | (6) |
| Arg—Lys—D—Asp, | (7) |
| Arg—Lys—D—Asp—Val, | (8) |
| Arg—Lys—Asp—D—Val, | (9) |
| D—Arg—Lys—Asp—Val, | (10) |
| Arg—D—Lys—Asp—Val, | (11) |
| Lys(Arg)—Asp, | (12) |
| Lys(Arg)—D—Asp | (13) |
| Arg—Lys(Arg)—Asp, | (14) |
| Arg—Lys—Asp(Val), | (15) |
| Arg—Lys—D—Asp(Val) | (16) | or a pharmaceutically acceptable acid addition salt thereof suppressing the function of the immune system.

2. A pharmaceutical composition suppressing the function of the immune system, which comprises as an active ingredient at least one peptide of the formulae (1) to (16) in free form or in the form of a pharmaceutically acceptable acid addition salt, as defined in claim 1 in a therapeutically effective amount in admixture with a pharmaceutically acceptable inert carrier.

3. D-Arg-Lys-D-Asp or a pharmaceutically acceptable acid addition salt thereof as defined in claim 1.

4. Arg-D-Lys-Asp or a pharmaceutically acceptable acid addition salt thereof as defined in claim 1.

5. D-Arg-Lys-Asp or a pharmaceutically acceptable acid addition salt thereof as defined in claim 1.

6. D-Arg-D-Lys-Asp or a pharmaceutically acceptable acid addition salt thereof as defined in claim 1.

7. Arg-Lys-D-Asp on a pharmaceutically acceptable acid addition salt thereof as defined in claim 1.

8. Lys-(Arg)-Asp or a pharmaceutically acceptable acid addition salt thereof as defined in claim 1.

9. Lys(Arg)-D-Asp or a pharmaceutically acceptable acid addition salt thereof as defined in claim 1.

* * * * *